United States Patent
Kindt et al.

(10) Patent No.: US 11,026,840 B2
(45) Date of Patent: Jun. 8, 2021

(54) OPHTHALMIC SURGERY METHOD

(71) Applicant: Carl Zeiss Meditec AG, Jena (DE)

(72) Inventors: Johannes Kindt, Weimar (DE); Manfred Dick, Gefell (DE); Mark Bischoff, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 98 days.

(21) Appl. No.: 16/300,017

(22) PCT Filed: May 9, 2017

(86) PCT No.: PCT/EP2017/061101
§ 371 (c)(1),
(2) Date: Nov. 8, 2018

(87) PCT Pub. No.: WO2017/194566
PCT Pub. Date: Nov. 16, 2017

(65) Prior Publication Data
US 2019/0142638 A1 May 16, 2019

(30) Foreign Application Priority Data
May 10, 2016 (DE) ...................... 10 2016 208 011.3

(51) Int. Cl.
*A61F 9/008* (2006.01)
*G16H 20/40* (2018.01)
*G16H 40/63* (2018.01)

(52) U.S. Cl.
CPC ...... *A61F 9/00827* (2013.01); *A61F 9/00836* (2013.01); *G16H 20/40* (2018.01);
(Continued)

(58) Field of Classification Search
CPC .............. A61F 9/00827; A61F 9/00836; A61F 2009/00842; A61F 2009/00872; A61F 2009/00878; G16H 20/40; G16H 20/63
(Continued)

(56) References Cited

U.S. PATENT DOCUMENTS 5,656,186 A  8/1997  Mourou et al.
6,648,877 B1 *  11/2003  Juhasz .................... A61F 9/008
                                                                606/10
(Continued)

FOREIGN PATENT DOCUMENTS

DE      41 31 361 A1    3/1993
DE      695 00 997 T2   4/1998
(Continued)

*Primary Examiner* — Nathan J Jenness
(74) *Attorney, Agent, or Firm* — Christensen, Fonder, Dardi & Herbert PLLC

(57) ABSTRACT

A planning device for generating control data for a treatment apparatus which by means of a laser device produces at least one incision surface in the cornea, and to a treatment apparatus having such a planning device. The invention further relates to a method for generating control data for a treatment apparatus which by using a laser device produces at least one incision surface in the cornea, and to a corresponding ophthalmic surgery method. The planning device is thereby provided with calculation means for defining the corneal incision surfaces, wherein the calculation means determine the corneal incision surfaces on the basis of data of a LIRIC structure and/or a refractive correction, and generate for the corneal incision surfaces a control data set for controlling the laser device, wherein the calculation means determine the corneal incision surfaces in such a manner that the LIRIC structure is enclosed by the incision surfaces.

12 Claims, 4 Drawing Sheets

(52) U.S. Cl.
 CPC .... *G16H 40/63* (2018.01); *A61F 2009/00842* (2013.01); *A61F 2009/00872* (2013.01); *A61F 2009/00878* (2013.01)

(58) Field of Classification Search
 USPC ........................................................ 606/4–6
 See application file for complete search history.

(56) References Cited

U.S. PATENT DOCUMENTS

| | | | |
|---|---|---|---|
| 8,486,055 B2 | 7/2013 | Knox et al. | |
| 9,408,747 B2* | 8/2016 | Wottke | A61F 9/00827 |
| 10,251,785 B2* | 4/2019 | Bischoff | A61F 9/00827 |
| 2006/0106371 A1 | 5/2006 | Muhlhoff et al. | |
| 2008/0183159 A1 | 7/2008 | Preuss et al. | |
| 2008/0275433 A1 | 11/2008 | Russmann et al. | |
| 2008/0319464 A1* | 12/2008 | Bischoff | A61F 9/00836 606/166 |
| 2012/0016351 A1 | 1/2012 | Stobrawa et al. | |
| 2014/0081249 A1* | 3/2014 | Bischoff | A61F 9/00804 606/5 |
| 2015/0335477 A1 | 11/2015 | Schuele et al. | |

FOREIGN PATENT DOCUMENTS

| | | |
|---|---|---|
| DE | 199 43 723 A1 | 4/2001 |
| DE | 199 43 735 A1 | 5/2001 |
| DE | 103 23 422 A1 | 4/2004 |
| DE | 10 2005 040 338 A1 | 3/2007 |
| DE | 10 2007 019 813 A1 | 10/2008 |
| DE | 10 2007 019 814 A1 | 10/2008 |
| DE | 10 2009 005 482 A1 | 7/2010 |

\* cited by examiner

OPHTHALMIC SURGERY METHOD

PRIORITY CLAIM

The present application is a National Phase entry of PCT Application No. PCT/EP2017/061101, filed May 9, 2017, which claims priority from German Application Number 102016208011.3 filed May 10, 2016, the disclosures of which are hereby incorporated by reference herein in their entirety.

FIELD OF THE INVENTION

The invention relates to a planning device for producing control data for a treatment apparatus, which produces at least one cut surface in the cornea by means of a laser device. The invention further relates to a treatment apparatus comprising a planning device of the aforementioned type.

The invention further relates to a method for producing control data for a treatment apparatus, which produces at least one cut surface in the cornea by means of a laser device.

Finally, the invention likewise relates to a method for eye surgery, wherein at least one cut surface in the cornea is produced by means of a treatment apparatus with a laser device.

BACKGROUND OF THE INVENTION

The prior art has disclosed very different treatment methods that have the correction of refraction at the human eye as a target. Here, the object of the surgical methods is to modify the cornea in a targeted manner in order thus to influence the light refraction in the eye. A plurality of surgical methods are used to this end. The most widespread method is the so-called laser in situ keratomileusis, which is also abbreviated LASIK. Here, a corneal lamella is detached from the corneal surface on one side and folded to the side. This lamella can be detached by means of a mechanical microkeratome, or else by means of a so-called femtosecond laser keratome, as distributed by Intralase Corp., Irvine, USA, for example. After the lamella has been detached and folded to one side, the application of an excimer laser is provided in the LASIK surgery, said excimer laser removing the corneal tissue exposed in this way from under the lamella by ablation. After the corneal tissue, which originally lay under the corneal surface, has been evaporated from the surface in this way, the corneal lamella is folded back onto its original place again.

The application of a laser keratome for exposing the lamella is advantageous over a mechanical knife since the geometric precision is improved and the frequency of clinically relevant complications is reduced. In particular, the lamella can be produced with a very much more constant thickness if laser radiation is used. Additionally, the cut edge is formed precisely, which reduces the risk of an impairment to healing as a result of this boundary that also still remains after the operation. However, a disadvantage of this method is that two different treatment apparatuses have to be used, namely, firstly, the laser keratome for exposing the lamella and, secondly, the laser that evaporates the corneal tissue.

These disadvantages have been remedied in a method which was recently implemented by Carl Zeiss Meditec AG and which is abbreviated by FLEx (femtosecond lenticule extraction). In this method for lenticule extraction, a cut geometry which separates a corneal volume (a so-called lenticule) in the cornea is formed in the cornea of the eye by means of a short-pulse laser, preferably a femtosecond laser. Said lenticule is then manually removed by the surgeon after the lamella covering the lenticule has been folded to the side. The advantage of this method lies in the fact that, firstly, the cut quality is once again improved by applying the femtosecond laser in combination with a curved contact glass.

Secondly, only one treatment apparatus is required; the excimer laser is no longer used. This method also avoids the risks and limitations of the excimer laser.

These days, a development of the FLEx method is referred to in the literature as the SMILE method; here, it is no longer a flap that is produced but only small opening incision as an access to the lenticule that lies under the so-called cap. The separated lenticule is removed through this small opening incision, as a result of which the biomechanical integrity of the front cornea is impaired less than in the case of LASIK or similar methods. Additionally, fewer nerve fibers in the cornea are severed near the surface in this way, which probably has an advantageous effect on the re-establishment of the original sensitivity of the corneal surface. The symptom of dry eyes, which often has to be treated after LASIK, is thereby reduced in terms of its manifestation and duration. Other complications after LASIK, too, which are usually in connection with the flap (e.g., flap displacement, folds, epithelial growth in the flap bed), occur less frequently without a flap.

When producing cut surfaces in the cornea by means of laser radiation, the optical radiation effect is usually exploited by virtue of an optical breakdown being produced by individual optical pulses, the duration of which may lie between approximately 100 fs and 100 ns. In addition, the practice of introducing individual pulses, whose energy lies below a threshold for an optical breakdown, into the tissue or material with such overlay that this also achieves a material or tissue separation is known. This concept of producing cuts in the corneal tissue allows a large variety of cuts.

Moreover, it is known that the corneal tissue can be modified by means of laser radiation in such a way that there is a local refractive power change despite the transparency being maintained (DE 41 31 361, DE 199 43 723 and DE 199 43 735 by the applicant, U.S. Pat. No. 8,486,055 Knox et al.). Moreover, use of this effect to produce diffractive structures, which modify the imaging properties of the entire eye in such a way that an existing refractive error can be compensated, is known. Here, the refractive power change can be brought about by a change in the local refractive index of the corneal material, and also by mechanical changes (e.g., cross-linking of the collagen fibers in the cornea). These changes can be brought about both by direct interaction of the laser radiation with the tissue in the case of laser power below the threshold at which a breakdown is produced and by interaction of the laser radiation with substances introduced into the cornea. By way of example, photosensitizers (e.g., riboflavin), IOP-reducing (IOP=intraocular pressure) pharmaceuticals, antimycotics, antibiotics, stem cells or nanoparticles can be used as substances. Such methods are also referred to as LIRIC (laser induced refractive index change). In particular, LIRIC is brought about by virtue of laser radiation being focused into the treatment region and leading there to a change in the structure of the material, said structure change remaining permanently, keeping the material transparent and modifying the local refractive index of the material and hence the refractive power of the transparent tissue (cornea, lens). An advantage of this method could be that no tissue separations in the cornea have to be undertaken for the purposes of correcting the refractive error. On the other hand, a very high accuracy is required when positioning the laser focus, for the purposes of which, in general, the eye has to be immobilized by means of suction to a contact element.

Mistakes may however also arise when carrying out the LIRIC method; in particular, the following are possible:
planning mistakes,
treatment mistakes as a result of
centration errors,
slippage as a result of missing, interrupted or insufficient immobilization,
a treatment termination as a result of an interruption of the immobilization,
a treatment termination as a result of a technical failure of the apparatus,
clinical side effects (e.g., increase in scattering or absorption),
regression of the correction,
progression of the refractive error,
unhappiness of the patient with the result of the treatment.

In theory, the LIRIC method also can be used to correct the treatment result; however, this requires precise positioning of the second treatment in relation to the first treatment (the first treatment finishes with the immobilization being released). If the first treatment itself already (intrinsically) has incorrect positioning because there has been slippage, for example, a repair can become very complicated. Possibly, the diffraction structure produced must then be "deleted" by exploiting the saturation of the treatment effect by virtue of untreated regions also being treated. Here, in a best-case scenario, a completely treated region without the intended refractive effect remains; however, this may cause increased side effects such as scattering, etc.

SUMMARY OF THE INVENTION

The invention is therefore based on the object of specifying a planning device for producing control data, a treatment apparatus for refraction-correcting eye surgery and a method for producing control data for such a treatment apparatus, which is able to modify a structure produced by means of LIRIC, which causes an unintended effect, in such a way that the unintended effect is removed. It would be advantageous if the originally intended effect of the LIRIC structure would be obtained simultaneously or thereafter.

According to the invention, this object is achieved by a planning device of the type set forth at the outset, said planning device having calculation means, which may include a computer, for setting or determining corneal cut surfaces, wherein the calculation means determine the cut surfaces in such a way that a lenticule is formed, the latter spatially reaching around (circumscribing, enclosing) the structure produced by means of LIRIC such that said structure, in entirety thereof, likewise can be removed from the cornea, together with the removal of the lenticule from the cornea.

Further, the invention is achieved by a treatment apparatus having a laser device, which separates at least one cut surface in the cornea by means of laser radiation in accordance with control data, and a planning device of the type just specified above for producing the control data, wherein the planning device determines the cut surfaces in such a way that a lenticule is formed, the latter circumscribing the structure produced by means of LIRIC such that said structure, in the entirety thereof, can be removed from the cornea.

Finally, the invention is likewise achieved by a method for producing control data according to the type set forth at the outset, said method including: producing a control data record for the corneal cut surface for actuating the laser device, wherein the planning device determines the cut surfaces in such a way that a lenticule is formed, the latter circumscribing the structure produced by means of LIRIC such that said structure, in the entirety thereof, can be removed from the cornea.

Finally, the invention is likewise achieved by a method, including: producing a control data record for the corneal cut surface, transmitting the control data to the treatment apparatus and producing the cut surfaces by actuating the laser device with the control data record, wherein, when producing the control data record, the cut surfaces are determined in such a way that a lenticule is formed, the latter circumscribing the structure produced by means of LIRIC such that said structure, in the entirety thereof, can be removed from the cornea.

Here, in particular the lenticule can be formed in such a way that the originally intended refractive error correction results or sets in, for example by way of a corresponding change in the curvature of the corneal front side, after the removal of said lenticule from the cornea. It may be advantageous if cuts for the lenticule are already applied before carrying out the LIRIC method; alternatively, they can also only be introduced at a later stage, when necessary.

Here, the invention employs the prior art in relation to the extraction of a lenticule (with a defined refractive power) for the purposes of extracting a special lenticule (which is referred to below as an enhancement lenticule in order to provide a better distinction from the "conventional" lenticule for correcting the refractive power) for removing an unwanted URIC structure. In a special variant, the invention contains the method of producing an enhancement lenticule which completely encloses the LIRIC structure to be removed. Thus, by removing the enhancement lenticule, the LIRIC structure is removed from the eye to the desired extent. This is implemented for the purposes of once again changing the optical properties of the eye.

In order to obtain a high level of safety for the patient, the form of the enhancement lenticule is selected in such a way that the removal thereof would not lead to an unacceptable refractive result of the treatment. Thus, the enhancement lenticule can be removed by surgery without great outlay for the user in order thus to remove the LIRIC structure from the eye; at the same time, the removal can attain an advantageous (or at least acceptable) refractive effect. In particular, the form of the enhancement lenticule can be adapted by means of lenticule extraction (SMILE) for refractive correction of a manifest visual defect of the eye. However, in special cases, enhancement lenticules with a geometry that precisely does not bring about a refractive change due to their form are also possible. These have an approximately constant thickness but have a certain profile curve which, in the case of the removal thereof, precisely does not insubstantially change the refractive power of the cornea.

Advantageously, an enhancement lenticule is already at least partly produced within the scope of the LIRIC treatment: a preventative enhancement lenticule. By way of example, the lenticule cut can already be introduced posteriorly in relation to the LIRIC structure before the LIRIC structure modifies the tissue. Additionally, the cap cut or a flap cut also can already be introduced anteriorly to the RIS structure. The advantage of this method consists of there consequently being a high level of certainty with respect of to relative position of the structures and consists of a preclusion from the outset of the cut guidance being influenced by LIRIC structures.

The invention consists of a more general configuration within the scope of a method for producing a LIRIC structure in combination with at least one cut in the cornea. Should an ablating method be used to remove the defective LIRIC structure instead of a lenticule extraction, it may be advantageous to introduce a preventative enhancement cut, which may be a flap cut, in particular, already within the scope of the RIS treatment.

In its most general form, the invention consists of producing a preventative enhancement structure (PES), which is not necessary for the primary treatment but which, in the case of a second treatment, makes the latter easier to carry out or improves the effect thereof. This enhancement structure can have one of the manifestations that were already described above; however, otherwise, it may only be a mark, for example, which serves to determine the relative position of a second treatment in relation to the first treatment.

However, the enhancement structure may also only be produced after the introduction of the LIRIC structure. In addition to the general problem of correctly positioning the second treatment in relation to the first treatment, this is connected with the problem that, in particular, the LIRIC structure could have a bothersome effect on the production of the enhancement structure. This can be considered when guiding the cut by virtue of a pre-compensation of the effect of the LIRIC structure being implemented in such a way that precisely the intended treatment effect arises from the interaction of the second treatment with the present effect of the first treatment. However, under certain circumstances, this is more complicated than the preventative production of enhancement structures.

As well as introducing the enhancement structure in relation to the LIRIC structure, either beforehand or afterwards in time, provision is made, in a combined treatment, for the necessary treatment steps to be carried out in a spatial sequence from the rear side of the cornea to the front side of the cornea. What this ensures is that the ultrashort pulse laser radiation can always be introduced/focused in the corneal tissue through an untreated region, without having to take account of optical effects of a treatment carried out in advance.

Here, according to the invention, this method can resort to a universal laser system which can both carry out the LIRIC treatment and produce the enhancement structure. Thus, for example, the LIRIC treatment can be carried out using an ultrashort pulse laser system with a 405 nm wavelength that, at the same time, is able to perforate the corneal tissue and introduce the enhancement structure in a further mode of operation. Furthermore, provision may be made of a laser system with a wavelength in the short-wave spectral range of approximately 300-450 nm, necessary for an LIRIC treatment, and with a further wavelength range of approximately 800 nm-1070 nm for the introduction of the enhancement structure. By way of example, this laser system includes a switchable frequency multiplication such as frequency doubling (SHG—second harmonic generation) or THG (third harmonic generation). Furthermore, it is likewise possible according to the invention for the treatments to be carried out on different (laser) devices which are able to position the LIRIC structure and the enhancement structure in relation to one another by way of protocols that are defined in a platform-overarching manner.

Being able to position an enhancement lenticule relative to an LIRIC structure that is already present, the exact position of which, however, is unknown (e.g., on account of a mistake in an earlier LIRIC treatment) is a further desirable variant. To this end, the position of the LIRIC structure in the cornea is measured. For the purposes of observing and localizing the LIRIC structure, phase-contrast microscopy or OCT (optical coherence tomography) of structures close behind the LIRIC structure come into question (corneal stroma, endothelial cells, membranes) or else confocal or wide-field fluorescence microscopy of the stromas changed by the LIRIC. Scanning microscopy methods can make use of the same scanner as the treatment system for the SMILE or LIRIC method in the process.

In addition to the method according to the invention for preparing an enhancement structure for removing an LIRIC structure virtually without side effects, provision is likewise made according to the invention for intraoperative dosimetry of the individually produced LIRIC structure to be introduced. By way of example, this is based on, before and after the introduction of a local LIRIC structure, optical pachymetry of the cornea assigned to the local structure being performed, said optical pachymetry being able to measure a refractive index and/or change in thickness of the cornea at this position. Since these measurements then registered in sequence establish a relative value that is assigned to the LIRIC effect, there can be, on an individual basis, a very high measurement accuracy of the LIRIC effect by this pachymetry. Intra-operative dosimetry is provided in addition to pre- and post-operative pachymetric dosimetry. Preferably, pachymetry is provided with a highly resolving method of optical coherence tomography (OCT). Here, the point-wise A-scan is used as point pachymetry and the lateral B-scan resolution is used for spatial 3D dosimetry. A further option for dosimetry consists in the spatially resolved measurement of the autofluorescence of the cornea, which is excited by the treatment, or which is excited in a measurement focus, following the treatment focus, from a further light source.

Since LIRIC is a scanning method and successive treatment foci lie close together (e.g., 0.5-5 µm), with only small changes in the tissue properties being expected therebetween, the results of the online measurement can also be used in predictive fashion for correcting the treatment strength of the respective following treatment foci.

By means of the dosimetry, the individual treatment can be optimized online and a treatment result can be documented objectively.

In order to carry out the method, an apparatus is provided according to the invention, said apparatus being able to meet some or all of the objects listed below, for example using the means specified:

1. Calculation of the structure: the calculation of an LIRIC structure is not the subject matter of this invention; a description is found in U.S. Pat. No. 8,486,055, the content of which is herewith incorporated by reference. Calculating a lenticule form and the derivation of corresponding control signals is known from, e.g., DE 10 2009 005 482, the content of which is herewith incorporated by reference. To this end, provision is made of: input means for the quantities required for the calculation, and means for storing and calculating the desired lenticule geometry.

2. Introduction of the structure in the correct position: centration and navigation are objects that have already been solved in conjunction with other refractive treatments and which are therefore known per se. Immobilizing the patient's eye in the correct position on a vacuum fixation element, in particular, is important. The use of a contact glass is advantageous but not mandatory. A liquid interface can also be used. To this end, provision is made of a corresponding laser-optical system, means for calibrating the system, detecting the relative structures, tracking the laser foci, OCT for the calibration of the transformation onto the eye geometry that has been modified by the fixation element (analysis of the distortion of pre-operation pachymetry and inclusion in the planning for the treatment foci).

3. Definition of coordinate systems and referencing of these to one another: this solution to this problem is already known for the production of lenticules or the navigation when using contact glasses (contact glass detection) and liquid interfaces (for example, from DE 10 2009 005 482). The relative position relation between LIRIC structure and enhancement lenticule (general enhancement structure or preventative enhancement structure) can easily be ensured by the invention if the correct position relation is produced by simultaneous introduction of the LIRIC structure and the preventative enhancement structure.

4. Registration by producing and processing registration data.

5. Deformation transformations: transforming to the eye geometry modified by the fixation element by taking account of the contact glass geometry and natural eye geometry. To this end, provision is made of: means for storage and calculation.

6. Monitoring of the treatment: illumination (in the infrared and/or visual spectral range) and observation, OCT, possibly confocal detection (see DE 103 23 422).

7. Detection: carried along detection by virtue of using partial beams for reference purposes (e.g., phase-contrast microscopy).

8. Logging: incremental logging of the advance.

9. Safety functions: to this end, provision is made of: power regulation, reference mark production, safety shutdown.

10. Resumption of an interrupted treatment: defining compensation writing layers for resuming the treatment after a possibly necessary interruption.

11. Evaluation of log information: using the available information about the first treatment within the scope of the treatment planning in the case of a resumption.

12. Detection: making use of post-operation pachymetry vs pre-operation pachymetry to measure the wavefront change intraoperatively, scattering measurements of the refractive structure.

13. Introduction of the second treatment in the correct position by evaluating reference marks.

14. Processing of information about the primary treatment: iterative production of the overall effect, wherein the partial effects of preceding treatment phases are used to plan the subsequent phase (here, a treatment phase can be an individual treatment focus, a line or a partial region of treatment foci).

15. Detection: scattering measurement at the LIRIC structure.

It is understood that the features mentioned above and features yet to be explained below can be used not only in the specified combinations but also in other combinations or on their own, without departing from the scope of the present invention.

BRIEF DESCRIPTION OF THE DRAWINGS

Below, the invention will still be explained in more detail in exemplary fashion on the basis of the attached drawings, which also disclose features that are essential to the invention.

In detail.

DETAILED DESCRIPTION

Figure 1:
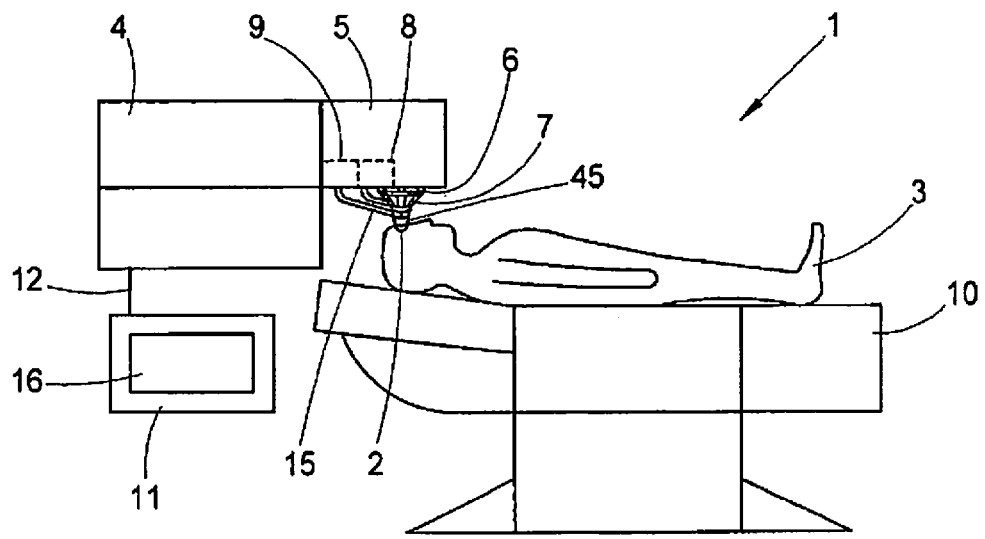
FIG. 1 shows a schematic illustration of a treatment apparatus with a planning device for a treatment in the case of eye-surgical refraction correction.

A treatment apparatus for eye surgery is illustrated in FIG. 1 and denoted by the general reference sign 1. The treatment apparatus 1 is embodied to introduce laser cuts on an eye 2 of a patient 3. To this end, the treatment apparatus 1 comprises a laser device 4, which emits a laser beam 6 from a laser source 5, said laser beam being directed into the eye 2 or the cornea of the eye as a focused beam 7. Preferably, the laser beam 6 is a pulsed laser beam with a wavelength of between 300 nanometers and 10 micrometers. Further, the pulse length of the laser beam 6 lies in the range between 1 femtosecond and 100 nanoseconds, wherein pulse repetition rates of 500 to 50 000 kilohertz and pulse energies between 0.01 microjoule and 0.01 millijoule are possible. Consequently, the treatment apparatus 1 produces a cut surface in the cornea of the eye 2 by way of deflection of the pulsed laser radiation. Therefore, a scanner 8 and a radiation intensity modulator 9 are also provided to this end in the laser device 4 or the laser source 5 thereof.

The patient 3 is situated on a couch 10, which is optionally adjustable in three spatial directions in order to align the eye 2 in a manner fitting to the incidence of the laser beam 6. The couch 10 is adjustable by motor in a preferred construction. As an alternative, the patient couch is less movable and, instead, the treatment apparatus is correspondingly adjustable by motor. In particular, actuation can be brought about by a controller 11 which, in principle, controls the operation of the treatment apparatus 1 and, to this end, is connected to the treatment apparatus by way of suitable data connections, connection lines 12, for example. Naturally, this communication can also be implemented in a different fashion, for example, by way of light guides or by radio. The controller 11 undertakes the corresponding settings and time control at the treatment apparatus 1, in particular the laser device 4 and consequently brings about corresponding functions of the treatment apparatus 1.

The treatment apparatus 1 further comprises an immobilization device 15, which immobilizes the position of the cornea of the eye 2 in relation to the laser device 4. This immobilization device 15 may comprise a contact glass 45, known per se, to which the cornea of the eye is applied by negative pressure and which impresses a desired geometric form on the cornea of the eye. Such contact glasses are known to a person skilled in the art from the prior art, for example from DE 102005040338 A1. To the extent that this relates to the description of the structure of the contact glass 45 that is available to the treatment apparatus 1, the disclosure of this document, DE 102005040338, is incorporated herein in the entirety thereof. Other modified or improved contact glass forms could also be advantageous for the invention and should therefore be included.

The treatment device 1 furthermore comprises a camera (not illustrated here), which is able to record an image of the cornea 17 of the eye through the contact glass 45. Here, the illumination for the camera can be implemented both in the visible and in the infrared range of light.

The controller 11 of the treatment apparatus 1 further comprises a planning device 16, which will still be explained in more detail below.

Figure 2:
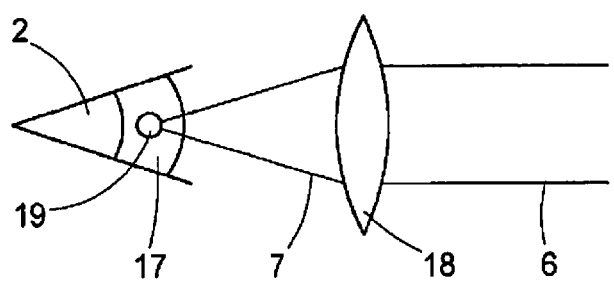
FIG. 2 shows a schematic illustration of the effect of the laser radiation that is used in the treatment apparatus of FIG. 1.

FIG. 2 schematically shows how the incident laser beam 6 acts. The laser beam 6 is focused and incident as the focused laser beam 7 in the cornea 17 of the eye 2. A schematically plotted optical unit 18 is provided for focusing purposes. It brings about a focus in the cornea 17, the laser radiation energy density being so high in said focus that, in combination with the pulse length of the pulsed laser radiation 6, a further nonlinear effect occurs in the cornea 17. By way of example, each pulse of the pulsed laser radiation 6 can produce an optical breakdown in the cornea 17 of the eye in the focus 19, said optical breakdown in turn initiating a plasma bubble that is only schematically indicated in FIG. 2. When the plasma bubble arises, the tissue layer separation comprises a larger area than the focus 19 even though the conditions for producing the optical breakdown are only achieved in the focus 19. So that an optical breakdown is produced by each laser pulse, the energy density, i.e., the fluence of the laser radiation, must lie above a certain, pulse-length-dependent threshold. A person skilled in the art knows of this relationship, for example from DE 69500997 T2. Alternatively, a tissue-separating effect can also be achieved by pulsed laser radiation by virtue of a plurality of laser radiation pulses being emitted in a region, with the focal spots overlapping. Then, a plurality of laser radiation pulses work together to obtain a tissue-separating effect. The type of tissue separation used by the treatment apparatus 1 is, however, of no further relevance to the description below; all that is essential is that a cut surface is generated in the cornea 17 of the eye 2.

The invention improves the pressure equalization in the region of the plasma bubbles while the latter are produced and thus improves the cut quality by reducing the tissue disturbance during the cutting process.

In order to carry out an eye-surgical refraction correction, a corneal volume is removed by means of laser radiation 6 from a region within the cornea 17 by virtue of tissue layers being separated therein, said tissue layers isolating the corneal volume and then facilitating the removal thereof. For the purposes of isolating the corneal volume to be removed, the position of the focus 19 of the focused laser radiation 7 in the cornea 17 is adjusted in the case of laser radiation that is introduced in pulsed fashion, for example. This is shown schematically in FIG. 3. The refractive properties of the cornea 17 are modified in a targeted manner by the removal of the volume in order thus to achieve the refraction correction. The volume is therefore usually lens-shaped and referred to as a lenticule.

Figure 3:
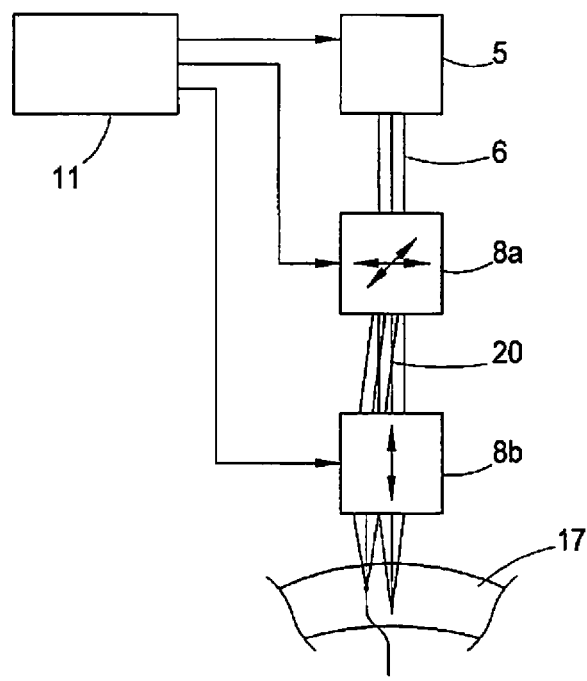
FIG. 3 shows a further schematic illustration of the treatment apparatus of FIG. 1 in respect of the introduction of the laser radiation.

In FIG. 3, the elements of the treatment apparatus 1 are only plotted to the extent that they are required for the understanding of the cut surface production. As already mentioned, the laser beam 6 is focused in a focus 19 in the cornea 17 and the position of the focus 19 in the cornea is adjusted such that, for the cut surface production, focused energy from laser radiation pulses is introduced into the tissue of the cornea 17 at different locations. The laser radiation 6 is preferably provided as pulsed radiation by the laser source 5. In the structure of FIG. 3, the scanner 8 is of two-part design and consists of an xy-scanner 8a, which is realized by two galvanometer mirrors that substantially deflect in orthogonal fashion in one variant. The scanner 8a deflects the laser beam 6 coming from the laser source 5 in two-dimensional fashion such that a deflected laser beam 20 is present after the scanner 8. Consequently, the scanner 8a brings about an adjustment in the position of the focus 19, substantially perpendicular to the principal direction of incidence of the laser beam 6 in the cornea 17. In addition to the xy-scanner 8a, a z-scanner 8b is also provided in the scanner 8 for the purposes of adjusting the depth position, said z-scanner being embodied as an adjustable telescope, for example. The z-scanner 8b ensures a change in the z-position of the position of the focus 19, i.e., the position thereof along the optical axis of incidence. The z-scanner 8b can be disposed upstream or downstream of the xy-scanner 8a. In order to produce the LIRIC structure, the laser source 5 can have a switchable embodiment with respect to the wavelength and/or power. The URIC structure is preferably written at 405 nm wavelength and a power of 0.01 to 2 nJ, while cuts are introduced at a wavelength of 1043 nm with a power of 50-250 nJ. This switchover is brought about by the controller 11.

The assignment of the individual coordinates to the spatial directions is not essential to the functional principle of the treatment apparatus 1, nor is it that the scanner 8a deflects about axes that are orthogonal to one another. Instead, use can be made of any scanner that is able to adjust the focus 19 in a plane not including the axis of incidence of the optical radiation. Further, it is also possible to use arbitrary non-Cartesian coordinate systems for deflecting or controlling the position of the focus 19. Examples to this end include spherical coordinates and cylindrical coordinates. The position of the focus 19 is controlled by means of the scanners 8a, 8b under actuation by the controller 11, which undertakes appropriate settings at the laser source 5, the modulator 9 (not shown in FIG. 3) and the scanner 8. The controller 11 ensures a suitable operation of the laser source 5 and the three-dimensional focus adjustment explained herein in exemplary fashion such that, ultimately, a cut surface is formed, said cut surface isolating a certain corneal volume that should be removed for the purposes of correcting the refraction.

The control device 11 operates according to predetermined control data that, for example, are predetermined as target points for the focus adjustment in the laser device 4 that is only explained in exemplary fashion here. As a rule, the control data are combined in a control data record. The latter yields geometric prescriptions for the cut surface to be formed, for example the coordinates of the target points as a pattern. Then, in this embodiment, the control data record also contains specific values for the focal position adjustment mechanism, e.g., for the scanner 8.

Figure 4:
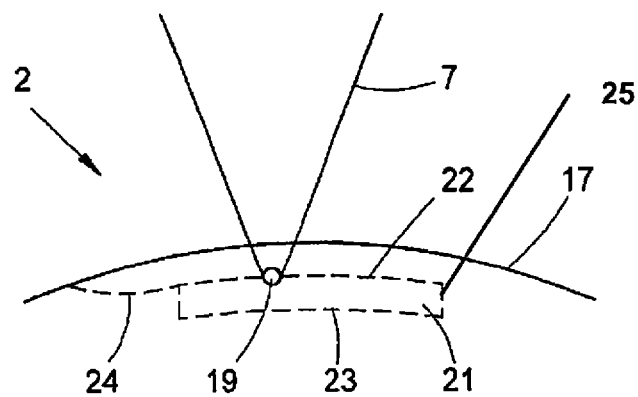
FIG. 4 shows a schematic sectional illustration through the cornea of an eye for elucidating the removal of the corneal volume in conjunction with the eye-surgical refraction correction.

Producing the cut surface with the treatment apparatus 1 is shown in FIG. 4 in exemplary fashion. A corneal volume 21 in the cornea 17 is isolated by adjusting the focus 19, in which the focused beam 7 is focused. To this end, cut surfaces are formed, said cut surfaces being formed here as an anterior flap cut surface 22 and as a posterior lenticule cut surface 23 in an exemplary fashion. These terms should only be understood in exemplary fashion here and should establish the relationship to the conventional LASIK or FLEx method, for which the treatment apparatus 1, as already mentioned above, is likewise embodied. All that is essential here is that the cut surfaces 22 and 23 and the circumferential side cut 25, which brings together the cut surfaces 22 and 23 at the edges thereof, isolate the corneal volume 21. By way of an opening incision 24, it is further possible to fold away a corneal lamella that delimits the corneal volume 21 in the anterior direction such that the corneal volume 21 is removable.

In an alternative and for the present invention essential manner, the SMILE method can be used; here, the corneal volume 21 is removed through a small opening incision, as described in DE 10 2007 019813 A1. The disclosure of this document, DE 10 2007 019813 A1, is incorporated here in the entirety thereof.

Figure 5:
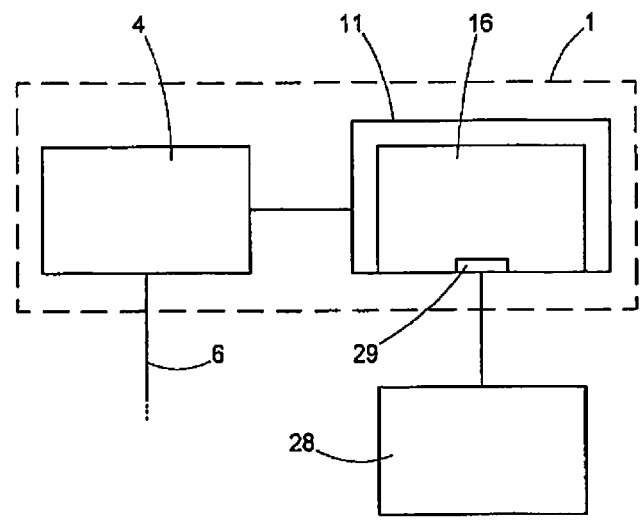
FIG. 5 shows a schematic illustration in respect of the construction of the treatment apparatus of FIG. 1, with particular reference to the planning device present there.

FIG. 5 schematically shows the treatment apparatus 1 and it will be used to explain the importance of the planning device 16 in more detail. In this variant, the treatment apparatus 1 comprises at least two devices or modules. The already-explained laser device 4 outputs the laser beam 6 onto the eye 2. Here, as already explained, the operation of the laser device 4 is fully automatic by way of the controller 11, i.e., the laser device 4 starts the production and deflection of the laser beam 6 following an appropriate activation signal and produces cut surfaces in the process, said cut surfaces being constructed as described above. The control signals required for the operation are received by the laser device 5 from the controller 11, the latter being provided with appropriate control data in advance. This is implemented by means of the planning device 16, which is shown in a purely exemplary manner as a constituent part of the controller 11 in FIG. 5. Naturally, the planning device 16 can also have an independent embodiment and can communicate with the control device 11 in a wired or wireless fashion. All that is essential in that case is that a corresponding data transmission channel is provided between the planning device 16 and the controller 11.

The planning device 16 produces a control data record which is made available to the controller 11 for the purposes of carrying out the eye-surgical refraction correction. Here, the planning device uses measurement data about the cornea of the eye. In the embodiment described here, these data originate from a measuring device 28, which had previously measured the eye 2 of the patient 3. Naturally, the measuring device 28 can be embodied in any way and transfer the appropriate data to the interface 29 of the planning device 16.

The planning device now assists the operator of the treatment apparatus 1 when setting the interface for isolating the corneal volume 21. This can go as far as fully automatically setting the cut surfaces, which may be brought about by virtue of, for example, the planning device 16 establishing the corneal volume 21 to be removed from the measurement data, defining the delimiting surfaces thereof as cut surfaces and producing appropriate control data for the controller 11 therefrom. At the other end of the degree of automation, the planning device 16 can provide input options at which a user enters the cut surfaces in the form of geometric parameters, etc. Intermediate stages provide suggestions for the cut surfaces, which are automatically generated by the planning device 16 and which are then modifiable by a user. In principle, all concepts that were already explained above in the more general part of the description can be used here in the planning device 16.

In order to carry out a treatment, the planning device 16 produces control data for the cut surface production, which then are used in the treatment apparatus 1.

Figure 6:
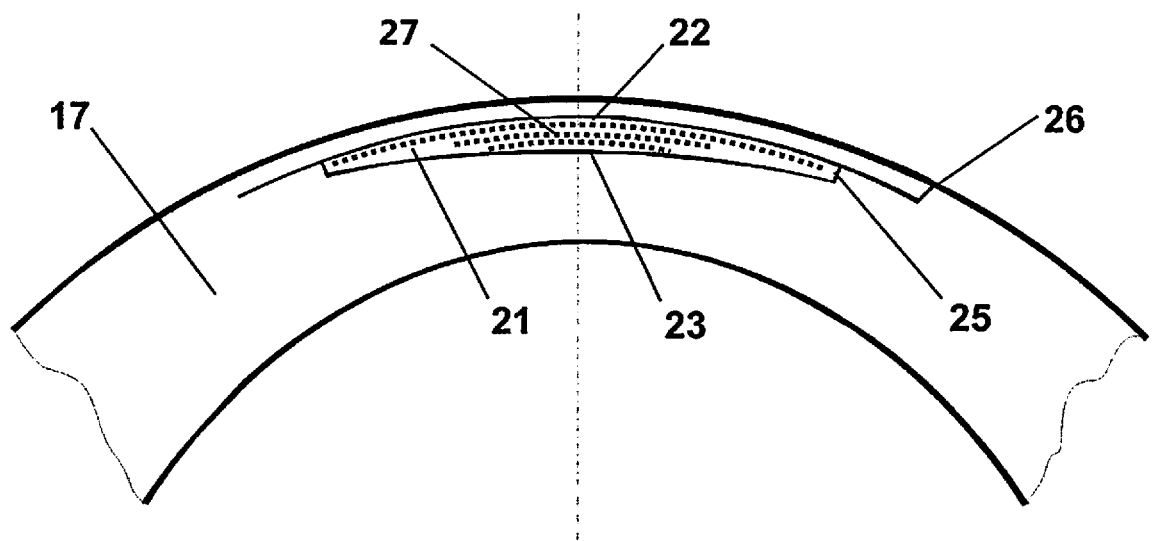
FIG. 6 shows a schematic illustration of a lenticule geometry according to the invention.
Figure 6:
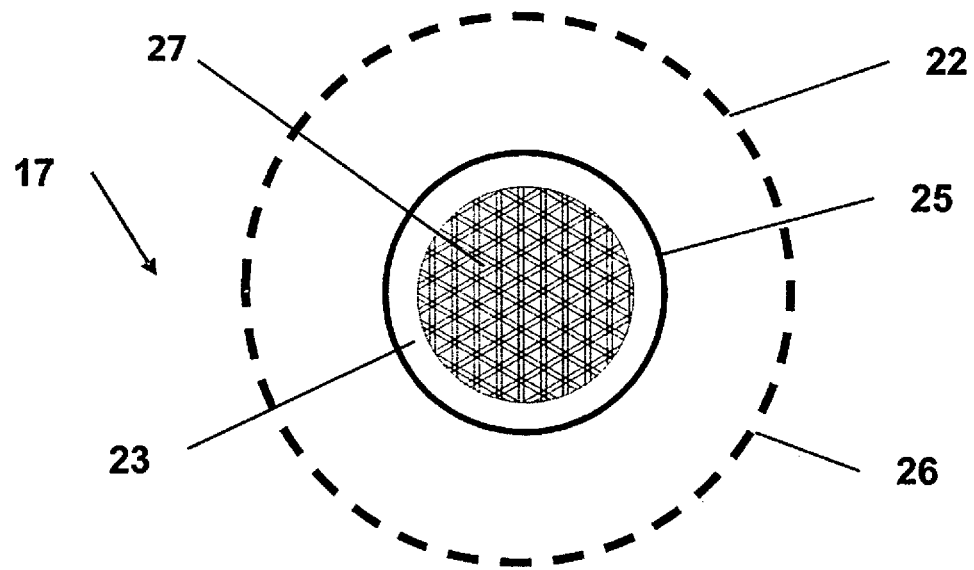

FIG. 6a shows a schematic illustration of a corneal cross section with an LIRIC structure 27 and the cut geometry of the lenticule enclosing the LIRIC structure. The cornea 17 has as an anterior cap cut 22 with an opening incision 26. The posterior lenticule cut 23 isolated the lenticule volume 21, which can be removed through the opening incision 26. If the lenticule structure is produced together with the LIRIC structure, it is also possible to dispense with the production of the opening incision 26 at this time and the latter is introduced only once it is necessary to remove the lenticule volume 21 with the LIRIC structure 27.

FIG. 6b shows a plan view of the cornea illustrated in FIG. 6a. The LIRIC structure 27 is completely surrounded by the lenticule volume 21 delimited by the cap cut 22, lenticule cut 23 and side cut 25; an opening incision is not illustrated here, for example because it need not be created immediately within the scope of the preventative enhancement structure.

Figure 7:
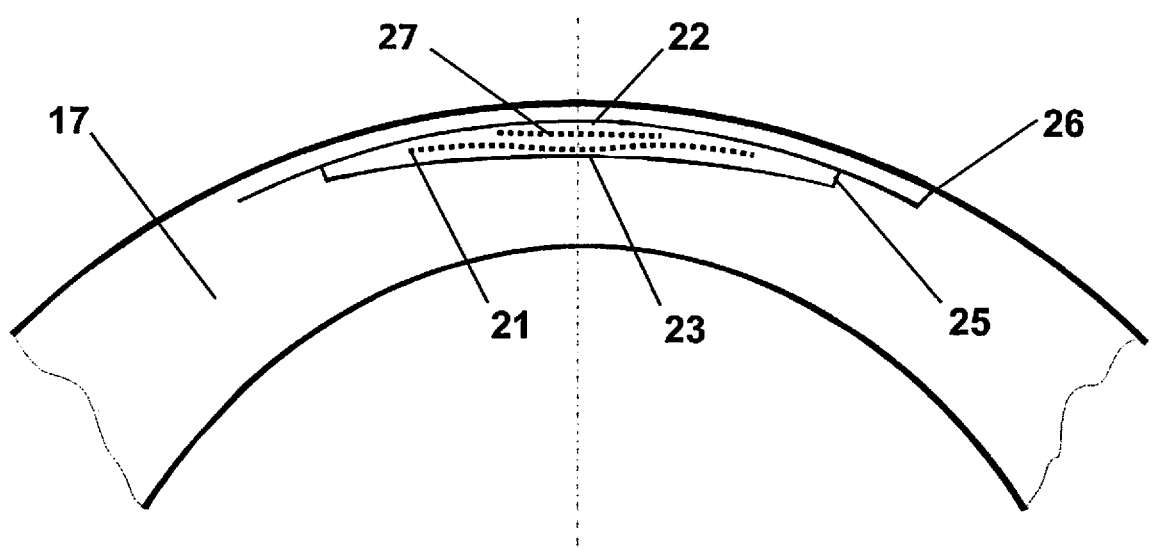
FIG. 7 shows another schematic illustration of a lenticule geometry according to the invention.

FIG. 7 shows a schematic illustration of a corneal cross section similar to FIG. 6a, with a different LIRIC structure 27 and the cut geometry of the lenticule enclosing the LIRIC structure. Here, the LIRIC structure 27 intrinsically has a 3-dimensional distribution of the refractive index modification.

Additionally, it should be noted that the treatment apparatus 1 or the planning device 16 naturally also specifically realizes the implementation of the method explained in general terms above.

A further embodiment of the planning device consists in the form of a computer program or a corresponding data medium with a computer program, which realizes the planning device on a corresponding computer such that the input of the measurement data is implemented by way of suitable data transmission means to the computer and the control data are transferred from this computer to the controller 11, for the purposes of which, once again, data transmission means known to a person skilled in the art come into question.

While the invention is illustrated in detail in the drawings and the description above, the illustration and description should be considered as explanatory or exemplary and as non-restrictive. It is understood that changes and modifications within the scope of the following claims can be undertaken by a person skilled in the art. In particular, the present invention comprises further embodiments with any combination of features of different embodiments described above and below.

The invention claimed is:

1. A treatment apparatus for eye surgery, comprising:
a laser device which produces at least one cut surface in the cornea by use of laser radiation in accordance with control data, and
a planning device for producing the control data, wherein the planning device comprises a computer configured to determine the at least one corneal cut surface on the basis of data of a laser induced refractive index change (LIRIC) structure, and, for the at least one corneal cut surface, produce a control data record for use in treating an eye of a Patient by actuating the laser device to produce the at least one corneal cut surface by making laser cuts on the eye based on the control data, and
wherein the computer is configured to determine the treatment of at least one corneal cut surface in such a way that the LIRIC structure is enclosed by the at least one cut surface, and the planning device is further configured to receive the data of the LIRIC structure and to transmit control data of the control data record to the laser device to enable the laser device to treat the eye by producing the at least one corneal cut surface that encloses the LIRIC structure when actuated.

2. The treatment apparatus as claimed in claim 1, wherein the at least one corneal cut surface isolates a lenticule which encloses the LIRIC structure.

3. The treatment apparatus as claimed in claim 1, wherein the at least one cut surface in the cornea isolates a lenticule which contains the LIRIC structure.

4. The treatment apparatus of claim 1, wherein the at least one corneal cut surface includes at least one of a cap cut and a lenticular cut.

5. The treatment apparatus of claim 1, wherein the planning device is further configured to transmit control data of the control data record to the laser device via a controller in communication with the planning device and the laser device.

6. A method for treating an eye by producing and communicating control data for a treatment apparatus for eye surgery, which produces cut surfaces in the cornea by means of a laser device, the method comprising the following steps:
receiving corneal data on the basis of data of a laser induced refractive index change (LIRIC) structure at a planning device;
determining the corneal cut surfaces, the corneal cut surfaces determined in such a way that the LIRIC structure is enclosed by the cut surfaces;
producing a control data record for use in treating an eye of a Patient by actuating the laser device to produce the corneal cut surfaces by making laser cuts on the eye based on the control data
transmitting control data of the control data record to the laser device so as to enable the laser device to treat the eye by producing the corneal cut surfaces that enclose the LIRIC structure when actuated; and
producing the cut surfaces by actuating the laser device with the control data record.

7. The method as claimed in claim 6, wherein the corneal cut surfaces isolate a lenticule which contains the LIRIC structure.

8. A non-transitory, tangible computer-readable storage medium storing computer program code, which, when executed on a computer, executes the method as claimed in claim 6.

9. The method of claim 6, wherein transmitting control data of the control data record for use by the laser device comprises transmitting control data of the control data record to the laser device via a controller in communication with the planning device and the laser device.

10. A method for eye surgery, wherein cut surfaces are produced in the cornea through the use of a treatment apparatus with a laser device, the method comprising the following steps:
providing corneal data on the basis of the data of a laser induced refractive index change (LIRIC) structure;
setting the corneal cut surfaces, the corneal cut surfaces comprising at least a lenticular cut and a cap cut, on the basis of the corneal data;
producing a control data record for the corneal cut surfaces;
transmitting the control data to the treatment apparatus; and
producing the cut surfaces by actuating the laser device with the control data record;
wherein the corneal cut a surfaces are determined in such a way that the LIRIC structure is enclosed by the cut surfaces.

11. The method as claimed in claim 10, wherein the corneal cut surfaces isolate a lenticule which contains the URIC structure.

12. A non-transitory, tangible computer-readable storage medium storing computer program code, which, when executed on a computer, executes the method as claimed in claim 10.

* * * * *

UNITED STATES PATENT AND TRADEMARK OFFICE
CERTIFICATE OF CORRECTION

PATENT NO. : 11,026,840 B2
APPLICATION NO. : 16/300017
DATED : June 8, 2021
INVENTOR(S) : Johannes Kindt et al.

Page 1 of 1

It is certified that error appears in the above-identified patent and that said Letters Patent is hereby corrected as shown below:

In the Specification

In Column 4, Line 20, delete "for example" and insert -- for example, --, therefor.

In Column 4, Line 32, delete "URIC" and insert -- LIRIC --, therefor.

In Column 4, Line 65, delete "to" and insert -- the --, therefor.

In Column 6, Line 46, delete "for example" and insert -- for example, --, therefor.

In Column 8, Line 64, delete "for example" and insert -- for example, --, therefor.

In Column 9, Line 31, delete "for example" and insert -- for example, --, therefor.

In Column 10, Line 20, delete "URIC" and insert -- LIRIC --, therefor.

In Column 10, Line 51, delete "for example" and insert -- for example, --, therefor.

In Column 12, Line 12, delete "for example" and insert -- for example, --, therefor.

In the Claims

In Column 12, Claim 1, Line 56, delete "Patient" and insert -- patient --, therefor.

In Column 13, Claim 6, Line 25, delete "Patient" and insert -- patient --, therefor.

In Column 13, Claim 6, Line 27, delete "data" and insert -- data; --, therefor.

In Column 14, Claim 11, Line 31, delete "URIC" and insert -- LIRIC --, therefor.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*